(12) United States Patent
Meyer et al.

(10) Patent No.: US 10,668,235 B2
(45) Date of Patent: Jun. 2, 2020

(54) OSCILLATING POSITIVE RESPIRATORY PRESSURE DEVICE

(71) Applicant: Trudell Medical International, London (CA)

(72) Inventors: Adam Meyer, Ontario (CA); Dan Engelbreth, Ontario (CA)

(73) Assignee: Trudell Medical International, London, Ontario (CA)

(*) Notice: Subject to any disclaimer, the term of this patent is extended or adjusted under 35 U.S.C. 154(b) by 632 days.

(21) Appl. No.: 15/415,524

(22) Filed: Jan. 25, 2017

(65) Prior Publication Data

US 2017/0128683 A1 May 11, 2017

Related U.S. Application Data

(63) Continuation of application No. 13/966,759, filed on Aug. 14, 2013, now Pat. No. 9,636,473, which is a
(Continued)

(51) Int. Cl.
*A61M 16/00* (2006.01)
*A61M 16/14* (2006.01)
(Continued)

(52) U.S. Cl.
CPC .... *A61M 16/0006* (2014.02); *A61M 16/0057* (2013.01); *A61M 16/0066* (2013.01);
(Continued)

(58) Field of Classification Search
None
See application file for complete search history.

(56) References Cited

U.S. PATENT DOCUMENTS

| 393,869 A | 12/1888 | Warren |
| 938,808 A | 11/1909 | Yount |

(Continued)

FOREIGN PATENT DOCUMENTS

| CN | 201329062 Y | 10/2009 |
| EP | 0 372 148 A1 | 6/1990 |

(Continued)

OTHER PUBLICATIONS

U.S. Appl. No. 15/819,150, filed Nov. 21, 2017, Meyer.
(Continued)

*Primary Examiner* — Rachel T Sippel
(74) *Attorney, Agent, or Firm* — Brinks Gilson & Lione

(57) ABSTRACT

An oscillating positive respiratory pressure apparatus and a method of performing oscillating positive respiratory pressure therapy. The apparatus includes a housing having an interior chamber, a chamber inlet, a chamber outlet, an exhalation flow path defined between the inlet and the outlet, and a restrictor member rotatably mounted within the interior chamber. The restrictor member has an axis of rotation that is substantially perpendicular to the flow path at the inlet, and includes at least one blocking segment. Rotation of the restrictor member moves the at least one blocking segment between an open position and a closed position. Respiratory pressure at the chamber inlet oscillates between a minimum when the at least one blocking segment is in the open position and a maximum when the at least one blocking segment is in the closed position. By exhaling into the apparatus, oscillating positive expiratory pressure therapy is administered.

26 Claims, 18 Drawing Sheets

Related U.S. Application Data continuation of application No. 12/472,215, filed on May 26, 2009, now Pat. No. 8,539,951.

(60) Provisional application No. 61/056,358, filed on May 27, 2008.

(51) Int. Cl.
  *A61M 16/20* (2006.01)
  *A61M 16/08* (2006.01)
  *A61M 11/06* (2006.01)

(52) U.S. Cl.
  CPC .... *A61M 16/0096* (2013.01); *A61M 16/0866* (2014.02); *A61M 16/14* (2013.01); *A61M 16/20* (2013.01); *A61M 16/208* (2013.01); *A61M 11/06* (2013.01); *A61M 16/0816* (2013.01)

(56) References Cited

U.S. PATENT DOCUMENTS

| | | |
|---|---|---|
| 2,670,739 A | 3/1954 | Ncneill |
| 2,918,917 A | 12/1959 | Emerson |
| 3,710,780 A | 1/1973 | Milch |
| 3,834,383 A | 9/1974 | Weigl et al. |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,253,651 A | 10/1993 | Stockwell et al. |
| 5,277,195 A | 1/1994 | Williams |
| 5,345,930 A | 9/1994 | Cardinal et al. |
| 5,372,128 A | 12/1994 | Haber et al. |
| 5,381,789 A | 1/1995 | Marquardt |
| 5,413,112 A | 5/1995 | Jansen et al. |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,613,497 A | 3/1997 | DeBush |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,727,546 A | 3/1998 | Clarke et al. |
| 5,791,339 A | 8/1998 | Winter |
| 5,816,246 A | 10/1998 | Mirza |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 6,026,807 A | 2/2000 | Puderbaugh et al. |
| 6,029,661 A | 2/2000 | Whaley et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| 6,182,657 B1 | 2/2001 | Brydon et al. |
| D440,651 S | 4/2001 | Foran |
| 6,240,917 B1 | 6/2001 | Andrade |
| 6,253,766 B1 | 7/2001 | Niles |
| 6,269,839 B1 | 8/2001 | Wickham et al. |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,446,629 B1 | 9/2002 | Takaki et al. |
| 6,447,459 B1 | 9/2002 | Larom |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,607,008 B1 | 8/2003 | Yoshimoto et al. |
| 6,615,831 B1 | 9/2003 | Truitt |
| 6,631,721 B1 | 10/2003 | Salter et al. |
| 6,659,100 B2 | 12/2003 | O'Rourke |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,889,564 B1 | 5/2005 | Marcotte et al. |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Sumners et al. |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |
| 7,856,979 B2 | 12/2010 | Doshi |
| 7,905,228 B2 | 3/2011 | Blacker et al. |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Abrammerovich et al. |
| 8,051,854 B2 | 11/2011 | Faram |
| RE43,174 E | 2/2012 | Schmidt et al. |
| 8,118,024 B2 | 2/2012 | DeVries et al. |

(56) References Cited

U.S. PATENT DOCUMENTS

| | | |
|---|---|---|
| 8,118,713 B2 | 2/2012 | Foley et al. |
| 8,225,785 B2 | 7/2012 | Richards et al. |
| 8,327,849 B2 | 12/2012 | Grychowski et al. |
| 8,360,061 B2 | 1/2013 | Brown et al. |
| 8,460,223 B2 | 6/2013 | Huster et al. |
| 8,469,029 B2 | 6/2013 | Brown et al. |
| 8,485,179 B1 | 7/2013 | Meyer |
| 8,528,547 B2 | 9/2013 | Dunsmore et al. |
| 8,539,179 B1 | 9/2013 | Meyer et al. |
| 8,985,111 B2 | 3/2015 | Grychowski et al. |
| D731,050 S | 6/2015 | Meyer |
| 9,149,589 B2 | 10/2015 | Meyer et al. |
| 9,220,855 B2 | 12/2015 | Meyer |
| 9,808,588 B1 | 11/2017 | Meyer et al. |
| 2003/0015195 A1 | 1/2003 | Haaije de Boer et al. |
| 2007/0089740 A1 | 4/2007 | Baumert et al. |
| 2007/0259759 A1 | 11/2007 | Sumners et al. |
| 2008/0053456 A1 | 3/2008 | Brown et al. |
| 2008/0078383 A1 | 4/2008 | Richards et al. |
| 2008/0245368 A1 | 10/2008 | Dunsmore et al. |
| 2008/0257348 A1 | 10/2008 | Piper |
| 2009/0241949 A1 | 10/2009 | Smutney et al. |
| 2010/0101573 A1 | 4/2010 | Foley et al. |
| 2010/0139655 A1 | 7/2010 | Genosar |
| 2010/0307487 A1 | 12/2010 | Dunsmore et al. |
| 2011/0290240 A1 | 12/2011 | Meyer et al. |
| 2012/0097164 A1 | 4/2012 | Rozario et al. |
| 2012/0304988 A1 | 12/2012 | Meyer |
| 2013/0133649 A1 | 5/2013 | Grychowski et al. |
| 2013/0184619 A1 | 7/2013 | Von Hollen et al. |
| 2013/0312746 A1 | 11/2013 | Grychowski |
| 2014/0041657 A1 | 2/2014 | Meyer |
| 2014/0150790 A1 | 6/2014 | Meyer |
| 2015/0013671 A1 | 1/2015 | Costella et al. |
| 2015/0053209 A1 | 2/2015 | Meyer et al. |
| 2015/0151060 A1 | 2/2015 | Grychowski et al. |
| 2015/0224269 A1 | 8/2015 | Alizoti et al. |
| 2015/0297848 A1 | 10/2015 | Meyer et al. |
| 2015/0374939 A1 | 12/2015 | Meyer et al. |
| 2016/0136369 A1 | 5/2016 | Meyer et al. |
| 2017/0028161 A1 | 2/2017 | Meyer et al. |
| 2017/0049979 A1 | 2/2017 | Meyer et al. |

FOREIGN PATENT DOCUMENTS

| | | |
|---|---|---|
| EP | 0 678 306 A2 | 10/1995 |
| EP | 1435251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| JP | 2010-523220 A | 7/2010 |
| WO | WO 1989/03707 A1 | 5/1989 |
| WO | WO 1996/40376 | 12/1996 |
| WO | WO 1999/16490 | 4/1999 |
| WO | WO 2000/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2016/012740 | 1/2016 |

OTHER PUBLICATIONS

IPR2018-01025 Petition; *D R Burton Healthcare LLC* v. *Trudell Medical International*; Title: Oscillating Positive Respiratory Pressure Device; (94 pp).

*D R Burton Healthcare LLC* v. *Trudell Medical International*; "Patent Owner's Preliminary Response to Petition for Inter Partes Review"; Case No. IPR2018-01025, U.S. Pat. No. 9,808,588; Sep. 7, 2018; 107 pages.

*D R Burton Healthcare LLC* v. *Trudell Medical International*; "Declaration of Dr. William W. Durgin, Ph.D., in Support of Patent Owner's Preliminary Response to Petition for Inter Partes Review"; Case No. IPR2018-01025, U.S. Pat. No. 9,808,588; Trudell Medical Exhibit 2001-00001-2001-00217; 217 pages.

*D R Burton Healthcare LLC* v. *Trudell Medical International*; "Petitioner's Reply to Patent Owner Preliminary Response"; Case No. IPR2018-01025, U.S. Pat. No. 9,808,588 B1; Oct. 9, 2018; 16 pages.

*D R Burton Healthcare LLC* v. *Trudell Medical International*; "Decision Denying Institution of Inter Partes Review"; Case No. IPR2018-01025, U.S. Pat. No. 9,808,588 B1; Nov. 29, 2018; 32 pages.

U.S. Appl. No. 14/674,494, Mar. 31, 2015, Meyer et al.
U.S. Appl. No. 29/524,678, filed Apr. 22, 2015, Meyer et al.
U.S. Appl. No. 29/538,317, filed Sep. 2, 2015, Engelbreth et al.
U.S. Appl. No. 29/538,323, filed Sep. 2, 2015, Engelbreth et al.
U.S. Appl. No. 15/415,524, filed Jan. 25, 2017, Meyer et al.
U.S. Appl. No. 15/453,767, filed Mar. 8, 2017, Meyer et al.

Web page entitled Bronchial Hygiene, acapella Vibratory PEP Therapy System accessed from http://www.smiths-medical.com/catalog/bronchial-hygiene/acapella/acapella.html on Jul. 7, 2009.

Web page entitled Thayer Quake accessed from http://www.thayermedical.com/quake.htm on Jul. 7, 2009.

Human growth hormone, cortisol, and acid-base balance changes after hyperventilation and breath-holding; PubMed—indexed for Medline; Int J Sports Med., Dec. 1986; 7(6):311-5, Djarova T.

Bosco C, Cardinale M. & Tsarpela O (1999). Influence of vibration on mechanical power and electromyogram activity in human arm flexor muscles. Eur J Appl Physiol 79, 306-311.

David Sumners; Power Breathing and Strength; http://EzineArticles.com/972576 Published: Feb. 7, 2008.

Good Vibrations blog; http://vibrotraining.blogspot.com, Earliest posting Jan. 17, 2008.

Breathtaking News; More Youbreathe; Aug. 10, 2007.

PCT International Search Report for PCT/IB2012/001089, dated Oct. 5, 2012.

PCT International Written Opinion for PCT/IB2012/001089, dated Oct. 5, 2012.

OSCILLATING POSITIVE RESPIRATORY PRESSURE DEVICE

RELATED APPLICATIONS

This application is a continuation of U.S. application Ser. No. 13/966,759, filed on Aug. 14, 2013, pending, which is a continuation of U.S. application Ser. No. 12/472,215, filed on May 26, 2009, now U.S. Pat. No. 8,539,951, which claims the benefit of US Provisional Application No. 61/056,358, filed on May 27, 2008, all of which are incorporated herein by reference.

TECHNICAL FIELD

The present disclosure relates to a respiratory treatment device, and in particular, to an oscillating positive respiratory pressure device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

One type of therapy, utilizing oscillating positive expiratory pressure ("OPEP"), is often used to address this issue. OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most hospitalized patients, and such patients can assume responsibility for the administration of OPEP therapy throughout their hospitalization and also once they have returned home. To that end, a number of portable OPEP devices have been developed.

BRIEF SUMMARY

A portable OPEP device and a method of performing OPEP therapy are described herein. The OPEP device is configurable to maintain desired operating conditions. A user may adjust the oscillation frequency by simply replacing a component of the OPEP device, or by changing the speed at which that component rotates. Furthermore, administration of OPEP therapy with the device does not rely on the device's physical orientation or the ability of its user to manipulate the device during operation.

In one aspect, the OPEP device comprises a housing having an interior chamber, a chamber inlet in communication with the chamber, a chamber outlet in communication with the chamber, an exhalation flow path defined between the inlet and the outlet, and a restrictor member rotatably mounted within the interior chamber. The restrictor member has an axis of rotation substantially perpendicular to the exhalation flow path at the inlet, and includes at least one blocking segment. The restrictor member may be movable with respect to the inlet such that rotation of the restrictor member moves the at least one blocking segment between an open position where the flow path at the inlet is unrestricted and a closed position where the flow path at the inlet is restricted. The respiratory pressure at the chamber inlet oscillates between a minimum when the at least one blocking segment is in the open position and a maximum when the at least one blocking segment is in the closed position.

In another aspect, the OPEP device comprises a shaft connecting a source of rotational energy to the restrictor member. The source of rotational energy may also comprise a motor adapted to rotate the shaft.

In another aspect, the OPEP device includes a second restrictor member rotatably mounted within the interior chamber and operatively connected to the shaft, the second restrictor member having a at least one blocking segment. The shaft is moveable along its axis of rotation to position the second restrictor member with respect to the inlet such that rotation of the shaft moves the at least one blocking segment on the second restrictor member between the open position and the closed position. A number of blocking segments on the restrictor member and a number of blocking segments on the second restrictor member may be different.

In another aspect, the source of rotational energy comprises a turbine operatively connected to the restrictor member and adapted to rotate the restrictor member in response to receiving a flow of air. The OPEP device may also comprise a turbine housing surrounding the turbine, the turbine housing having a compressed air inlet configured to receive compressed air from a compressed air source and an exhaust outlet.

In yet another aspect, the OPEP device may be configured to simultaneously administer both OPEP and aerosol therapies. The OPEP device may include a respiratory portal in fluid communication with the inlet, the respiratory portal including a mouthpiece and a nebulizer port. The mouthpiece may be proximate the nebulizer port. An inhalation flow path is defined between the mouthpiece and the nebulizer port, wherein the inhalation flow path does not traverse the exhalation flow path defined between the inlet and the outlet.

In another aspect, the restrictor member is configured to rotate in response to exhaled air traversing the exhalation flow path. The at least one blocking segment is configured to move between the open position and the closed position independent of the exhalation pressure at the inlet. The restrictor member may also be removably mounted within the interior chamber.

In one embodiment, an OPEP device includes a housing having an interior chamber, a chamber inlet in communication with the chamber, a chamber outlet in communication with the chamber, an exhalation flow path defined between the inlet and the outlet, and a restrictor member rotatably mounted within the interior chamber, the restrictor member having at least one blocking segment and a plurality of vanes configured to rotate the restrictor member in response to exhaled air traversing the flow path. The restrictor member is positioned with respect to one of the inlet or the outlet such that rotation of the restrictor member moves the at least one blocking segment between an open position, where the exhalation flow path at the one of the inlet or the outlet is unrestricted, and a closed position, where the flow path at the one of the inlet or the outlet is restricted. The exhalation pressure at the chamber inlet oscillates between a minimum when the at least one blocking segment is in the open position and a maximum when the at least one blocking segment is in the closed position. The at least one blocking segment may have a cross-sectional area greater than a cross-sectional area of the one of the inlet or the outlet. The housing may include a one-way valve configured to allow air to enter the interior chamber through a valve opening. A center of gravity of the restrictor member may be radially offset from the axis of rotation of the restrictor member. The restrictor member may also be removably mounted within the interior chamber.

According to another aspect, a method of performing oscillating positive respiratory pressure therapy is provided. The method includes providing an oscillating positive respiratory pressure apparatus, which may consist of a housing defining an interior chamber, a chamber inlet in communication with the chamber, a chamber outlet in communication with the chamber, an exhalation flow path defined between the inlet and the outlet, and a restrictor member having at least one blocking segment and a plurality of vanes. The restrictor member is rotatably mounted in the interior chamber and positioned such that rotation of the restrictor member moves the at least one blocking segment between an open position where the exhalation flow path at one of the inlet or the outlet is unrestricted and a closed position where the exhalation flow path at the one of the inlet or outlet is restricted. The method may include receiving exhaled air through the inlet, rotating the restrictor member in response to receipt of the exhaled air at the plurality of vanes, and oscillating an exhalation pressure between a minimum and a maximum at the inlet during an exhalation period. The minimum may be achieved when the restrictor member is in the open position and the maximum may be achieved when the restrictor member is in the closed position. The restrictor member may be configured to move between the open position and the closed position independent of the exhalation pressure at the chamber inlet.

In yet another embodiment, a system for providing oscillating respiratory pressure therapy in combination with aerosol therapy is provided. The system may include an oscillating positive respiratory pressure apparatus having a housing defining a chamber, a chamber inlet in communication with the chamber, and a chamber outlet in communication with the chamber. An exhalation flow path is defined between the chamber inlet and the chamber outlet. A restrictor member having at least one blocking segment and a plurality of vanes is rotatably mounted in the interior chamber and positioned such that rotation of the restrictor member moves the at least one blocking segment between an open position where the exhalation flow path at one of the chamber inlet or the chamber outlet is unrestricted and a closed position where the exhalation flow path at the one of the chamber inlet or the chamber outlet is restricted. Also, a respiratory portal is adapted for receiving an aerosol medicament. The system may further include an aerosol therapy apparatus removably connected to the respiratory portal of the oscillating positive respiratory pressure apparatus. The aerosol therapy apparatus may consist of an aerosol housing having an aerosol chamber for holding an aerosol medicament and an aerosol outlet communicating with the aerosol chamber for permitting the aerosol medicament to be withdrawn from the aerosol chamber. The system may also have an inhalation flow path defined between the aerosol outlet and a user interface, where the inhalation flow path does not traverse the exhalation flow path defined between the chamber inlet and the chamber outlet. The aerosol medicament traverses the inhalation flow path without contacting the restrictor member.

DETAILED DESCRIPTION OF THE PRESENTLY PREFERRED EMBODIMENTS

OPEP therapy is very effective within a specific range of operating conditions. For example, an adult human may have an exhalation flow rate ranging from 10 to 60 liters per minute, and may maintain a static exhalation pressure in the range of 10 to 20 cm $H_2O$. Within these parameters, OPEP therapy is believed to be most effective when changes in the exhalation pressure range from 5 to 20 cm $H_2O$ oscillating at a frequency of 10 to 40 Hz. In contrast, an infant may have a much lower exhalation flow rate, and may maintain a lower static exhalation pressure, thereby altering the operating conditions most effective for OPEP therapy. As described below, the present invention is configurable so that ideal operating conditions may be selected and maintained.

Figure 1:
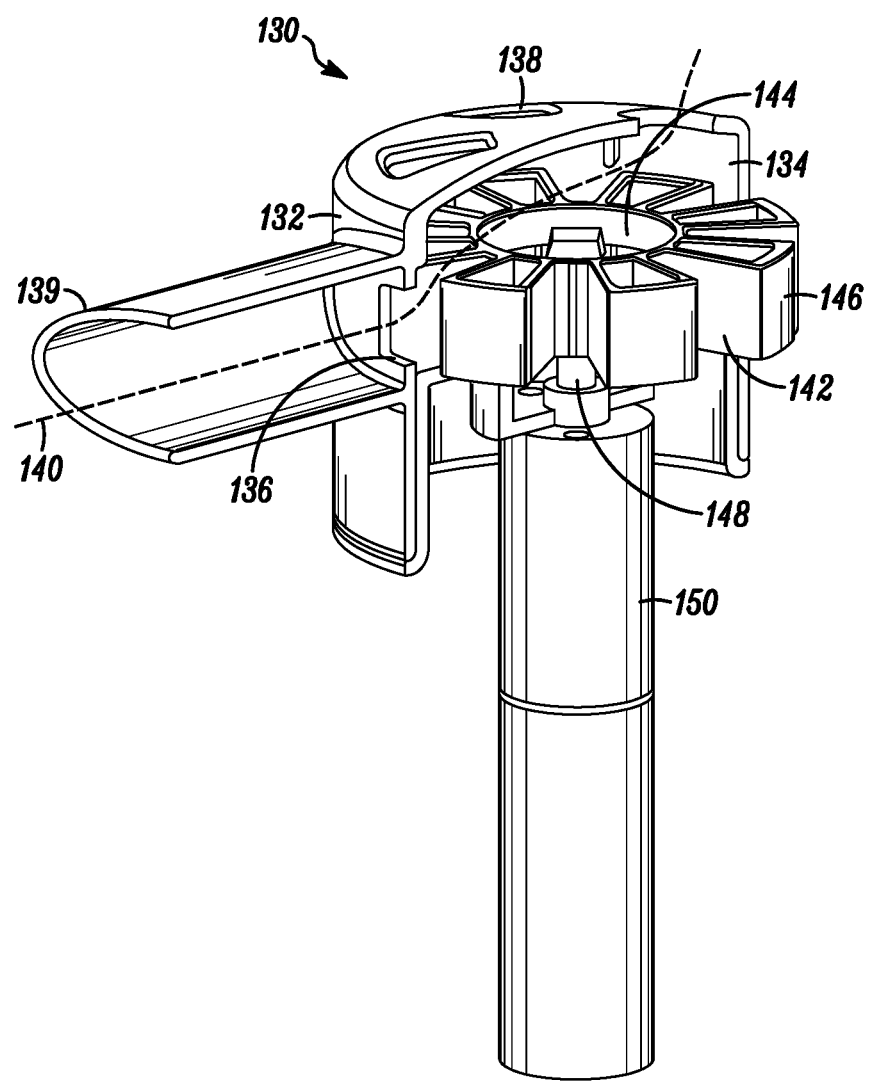
FIG. 1 is a perspective view of a first embodiment of an OPEP device with a side portion of the device's housing removed.

Referring to FIG. 1, a first embodiment of an OPEP device 130 is shown with a side portion of a housing 132 removed for purposes of illustration. In general, the OPEP device 130 comprises a housing 132 having an interior chamber 134, a chamber inlet 136, and a chamber outlet 138. An exhalation flow path 140 is defined through chamber inlet 136, the interior chamber 134, and the chamber outlet 138. The housing 132 may also be associated with a mouthpiece 139 for receiving exhaled air. Although the mouthpiece 139 is shown in FIG. 1. as being fixedly attached to the housing 132, it is envisioned that the mouthpiece 139 may be removable and replaceable with a mouthpiece 139 of a different shape or size. Alternatively, other user interfaces, such as breathing tubes or gas masks (not shown) may be associated with the housing 132. Preferably, the housing 132 is openable so that the interior chamber 134 and the parts contained therein can be periodically accessed, cleaned, and replaced. The housing 132 may be constructed of any durable material, such as a plastic or polymer.

In FIG. 1, the housing 132 and the interior chamber 134 are cylindrical. However, a housing of any shape could be used. Furthermore, the chamber inlet 136 is generally shown as being a single, rectangular inlet. However, the chamber inlet 136 could also be any shape or series of shapes, such as a plurality of circular inlets. More importantly, it should be appreciated that the cross-sectional area of the chamber inlet 136 influences the ideal operating conditions discussed above. Likewise, the chamber outlet 138 is generally shown as a plurality of apertures, however a single aperture or a number of arrangements of apertures may also be used. Although these variables are discussed in general with reference to the embodiment of FIG. 1, it should be understood that every embodiment described herein may be varied in a similar manner.

A restrictor member 142 is rotatably mounted within the interior chamber 134. The restrictor member 142 also may be constructed of any durable plastic or polymer, such as polypropylene. As shown in FIG. 1, the restrictor member 142 comprises a hub portion 144 and at least one blocking segment 146 extending outward from the hub portion 144. The restrictor member 142, however, could be any number of shapes, so long as it may be positionable such that at least one blocking segment 146 located on the restrictor member 142 is capable of at least partially blocking the chamber inlet 136, as described below.

The restrictor member 142 is connected at the hub portion 144 to a shaft 148, such that rotation of the shaft 148 causes rotation of the restrictor member 142. The shaft 148 extends through the housing 132 and may be operatively connected to a motor 150. The motor 150, along with batteries (not shown) for powering the motor 150, may be housed within a motor housing (not shown) attached to the OPEP device 130. Although it is preferred that the shaft 148 be adapted for connection to a motor 150, it is also envisioned that the shaft 148 could extend through the housing 132 and be adapted for manual rotation by the user of the OPEP device 130.

Figure 2:
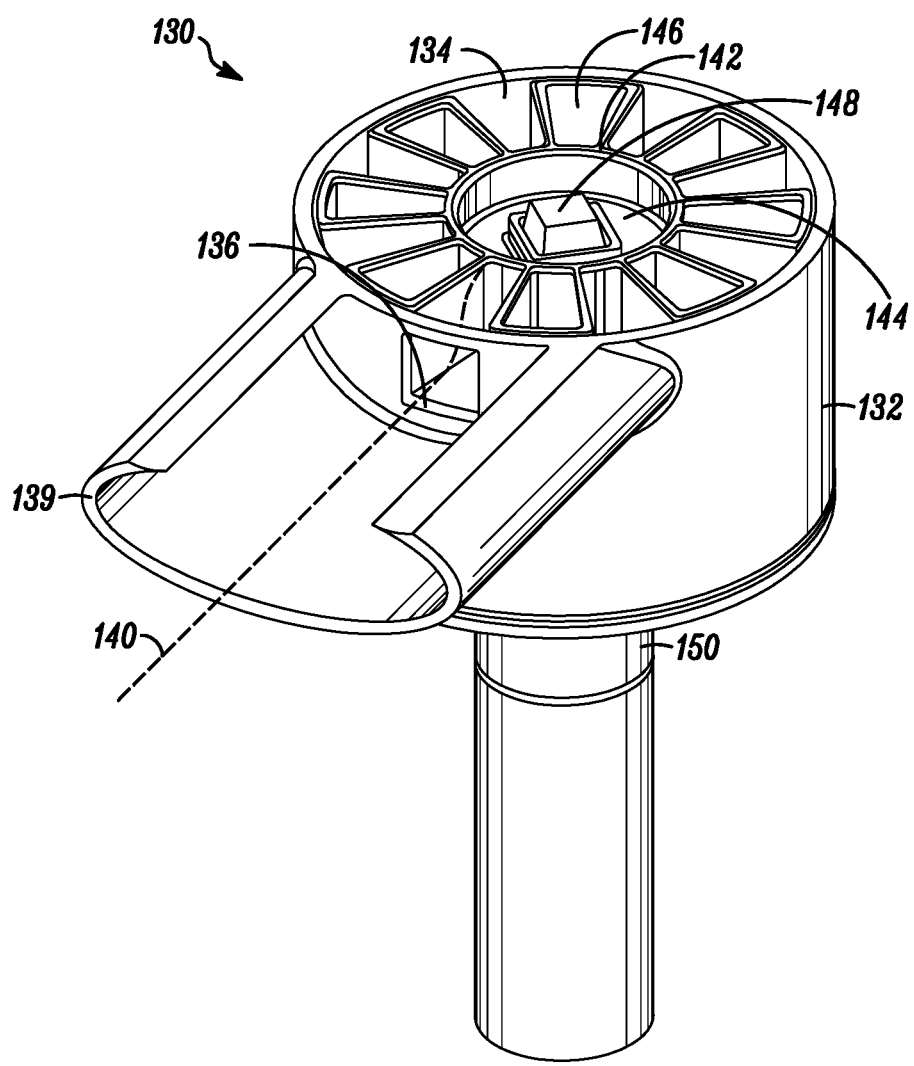
FIG. 2 is a perspective view of the embodiment of FIG. 1 with a top portion of the device's housing removed, showing a restrictor member in an open position.
Figure 3:
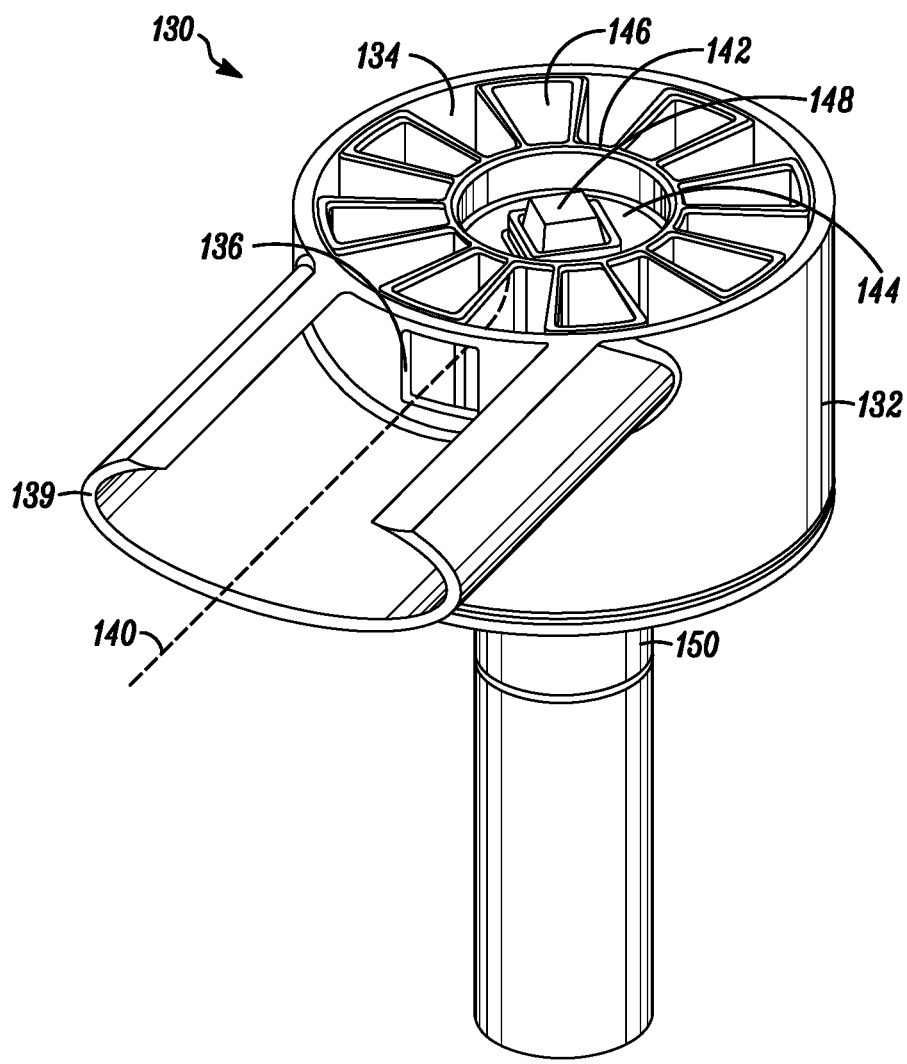
FIG. 3 is a perspective view of the embodiment of FIG. 1 with a top portion of the device's housing removed, showing a restrictor member in an intermediate position.
Figure 4:
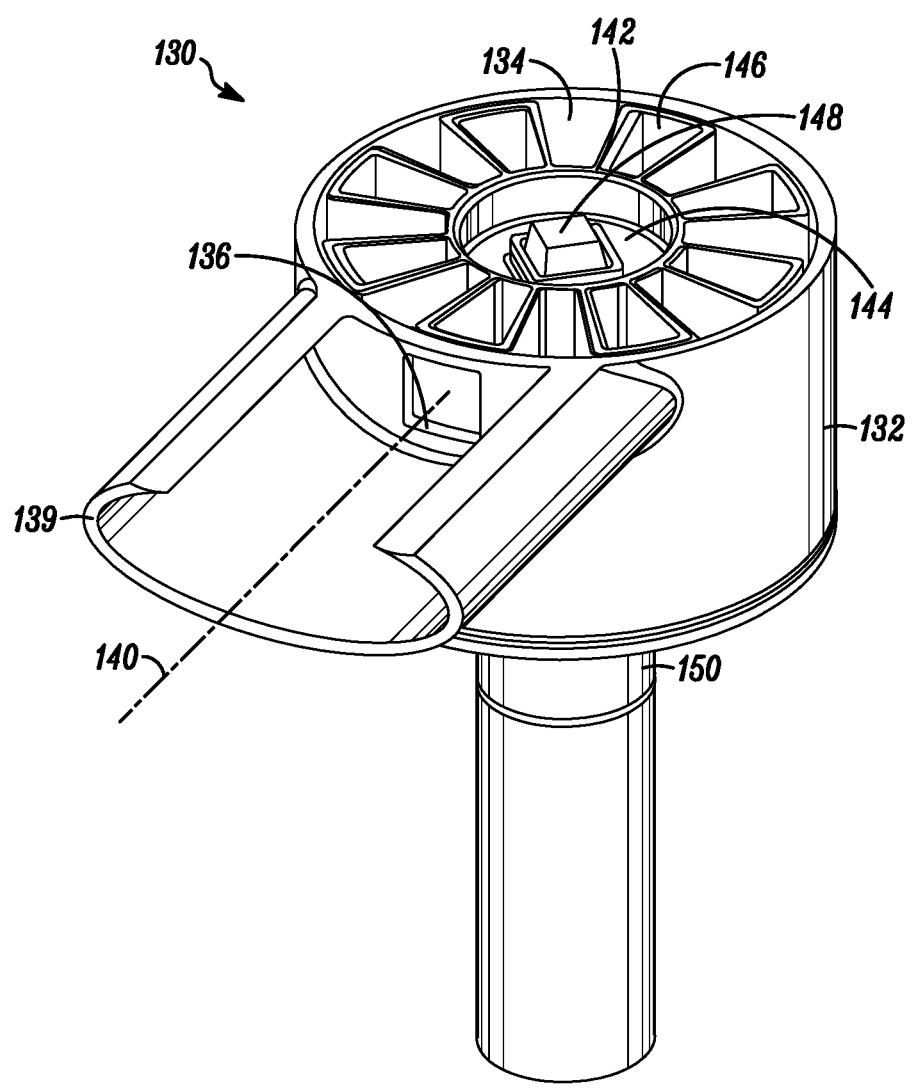
FIG. 4 is a perspective view of the embodiment of FIG. 1 with a top portion of the device's housing removed, showing a restrictor member in a closed position.
Figure 5A:
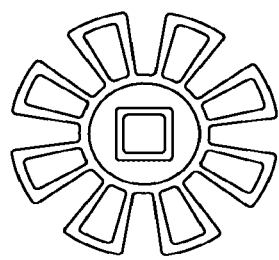
FIGS. 5A-E are top views of various restrictor members.
Figure 5B:
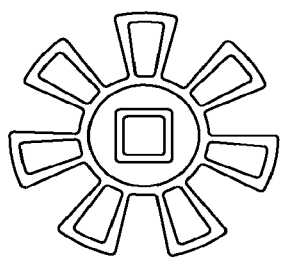
Figure 5C:
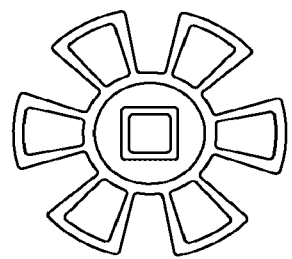
Figure 5D:
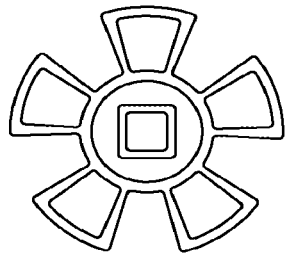
Figure 5E:
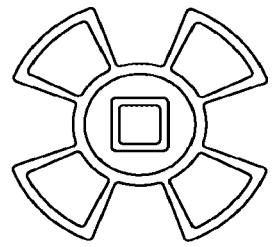

Referring to FIGS. 2-4, the OPEP device 130 is shown with a top portion of the housing 132 removed for purposes of illustration. In FIG. 2, the OPEP device 130 is shown with the restrictor member 142 and the chamber inlet 136 arranged in an open position. The restrictor member 142 is positioned in an open position when no blocking segment 146 is substantially blocking the chamber inlet 136 and when the flow path 140 through the cross-sectional area of the chamber inlet 136 is substantially unrestricted by the restrictor member 142. Thus, when the restrictor member 142 is in an open position, a user of the OPEP device 130 may freely exhale into the mouthpiece 139 and the exhaled air may travel along the exhalation flow path 140 through the chamber inlet 136, into the interior chamber 134, and out the chamber outlet 138. In the open position, the exhalation pressure at the chamber inlet 136 is at a minimum.

Referring to FIG. 3, the restrictor member 142 is shown in an intermediate position. The restrictor member 142 moves to an intermediate position when the restrictor member 142 is rotated to a position where a blocking segment 146 is at least partially blocking the chamber inlet 136 and the flow path 140 through the cross-sectional area of the chamber inlet 136 is at least partially restricted by the restrictor member 142. As a user exhales into the mouthpiece when the restrictor member 142 is in an intermediate position, the exhaled air passes through the unblocked portion of the flow path 140 and exits the interior chamber 134 through the chamber outlet 138. If the restrictor member 142 is in an intermediate position moving to an open position (FIG. 2), then the exhalation pressure at the chamber inlet 136 is decreasing. If the restrictor member 142 is moving to a closed position, the exhalation pressure at the chamber inlet 136 is increasing.

Referring to FIG. 4, the restrictor member 142 is shown in a closed position. The restrictor member 142 moves to a closed position when the restrictor member 142 is rotated to a position where a blocking segment 146 substantially blocks the chamber inlet 136 and the flow path 140 through the cross-sectional area of the chamber inlet 136 is substantially restricted by the restrictor member 142. Thus, when the restrictor member 142 is in a closed position, substantially no exhaled air passes through the chamber inlet 136. It should be understood that a complete seal need not be formed at the chamber inlet 136 between the restrictor member 142 and the housing 132. A small amount of exhaled air may be permitted to pass through the chamber inlet 136 when the restrictor member is in the closed position. Nevertheless, in the closed position, exhalation pressure at the chamber inlet 136 is at a maximum.

When the OPEP device 130 is in operation and the shaft 148 is continuously rotated, the restrictor member 142 moves between an open position, multiple intermediate positions, a closed position, multiple intermediate positions, and back to an open position. Likewise, the cross-sectional area of the flow path 140 through the chamber inlet 136 transitions from being substantially unrestricted, to substantially restricted, and back to being substantially restricted. As a result, when the user exhales into the mouthpiece 139, the exhalation pressure at the chamber inlet 136 increases to a maximum as the restrictor member 142 moves from an open position to a closed position and decreases to a minimum as the restrictor member 142 returns to an open position. As the restrictor member 142 continues to rotate and periodically restrict the flow path 140 through the chamber inlet 136, the exhalation pressure at the chamber inlet 136 oscillates between a minimum when the restrictor member 142 is in an open position and a maximum when the restrictor member 142 is in a closed position. This oscillating exhalation pressure effectively transmits an oscillating back pressure to the lungs, thereby splitting open obstructed airways, and loosening the secretions contributing to bronchial obstructions.

As previously stated, the housing 130 is preferably openable so that the restrictor member 142 may be accessed. The restrictor member 142 is removably connected to the shaft 148 such that a user can remove the restrictor member 142 for cleaning or replacement with a new or different restrictor member 142. Referring to FIGS. 5A-E, top views of multiple restrictor members 142 are shown. The hub portion 144 of each restrictor member 142 has a slot 145 keyed to fit on a corresponding keyed portion (not shown) of the shaft 148. In this regard, a user is able to easily remove an existing restrictor member 142 for cleaning or replacement with a new restrictor member 142.

Depending on the prescribed treatment, a user may select from a number of restrictor members 142, each having a different number of blocking segments 146. FIGS. 5A-E show an eight blocking segment 146 restrictor member 142 and multiple alternative restrictor members 142a, 142b, 142c, 142d, having anywhere from four to seven blocking segments 146. By changing the number of blocking segments 146 on the restrictor member 142, the user may change the oscillation frequency of the exhalation pressure generated at the chamber inlet 136 for a given rotation speed of the motor 150. Furthermore, the relative size or shape of the blocking segments 146 on a restrictor member 146 may vary, thus providing for added variation in the oscillation, if desired.

In addition, the motor 150 may be a variable speed motor controllable by the user. Although the motor may be configured to rotate the restrictor member back and forth in opposite directions, the restrictor member 142 is preferably only rotated in a single direction. By adjusting the rotational speed of the motor 150, a user may also adjust the oscillation frequency of the exhalation pressure generated at the chamber inlet 136. This combination of different restrictor members 142 and the variable speed motor 150 provides for a highly configurable OPEP device 130.

Figure 6:
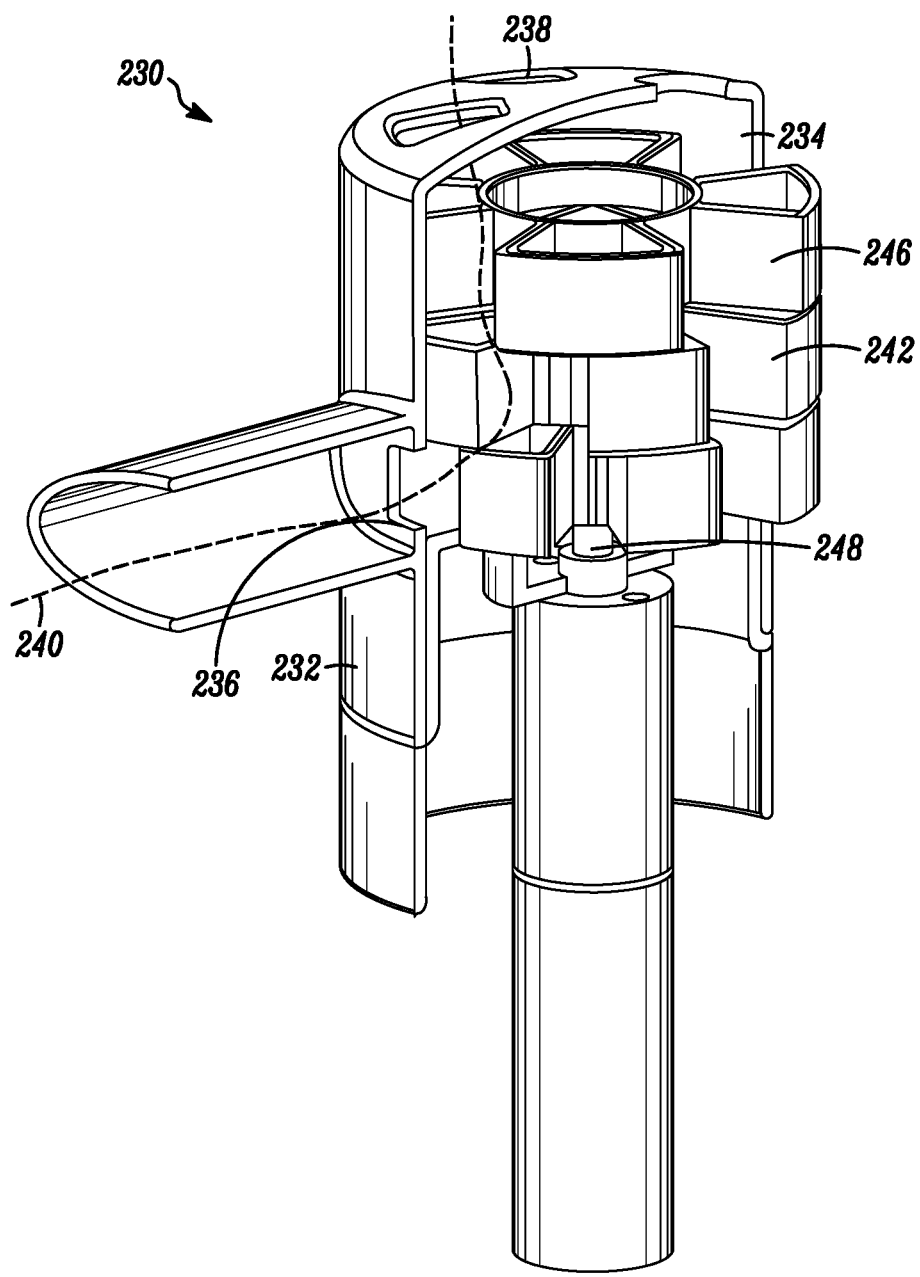
FIG. 6 is a perspective view of a second embodiment of an OPEP device with a side portion of the device's housing removed.

Referring to FIG. 6, a second embodiment of an OPEP device 230 is shown with a side portion of a housing 232 removed for purposes of illustration. In general, the OPEP device 230 has a larger housing 232 for accommodating multiple restrictor members 242. The housing 232 also has an interior chamber 234, a chamber inlet 236, and a chamber outlet 238. A flow path 240 is defined through the chamber inlet 236, the interior chamber 234, and exiting the chamber outlet 238.

Within the interior chamber 234, the restrictor members 242 may either be stacked atop one another and operatively connected to a shaft 248, or, in the alternative, each individually connected to the shaft 248. Furthermore, each restrictor member 242 may have a different number of blocking segments 246. As in the prior embodiment, the housing 232 is openable so that a user may remove and replace the restrictor member 242 positioned adjacent the chamber inlet 236. Thus, the interior chamber 232 may conveniently store multiple restrictor members 242 from which the user may choose to position on the shaft 248 adjacent the chamber inlet 236.

Alternatively, the shaft 248 may be moveable along its axis of rotation so that a user may position a different restrictor member 242 adjacent the chamber inlet 236 simply by sliding the shaft further in or out of the housing 232. Therefore, a user can adjust the oscillation frequency without opening the housing 232 and replacing the restrictor member 242 positioned adjacent the chamber inlet 236, and without adjusting the rotational velocity of the shaft 248.

Figure 7:
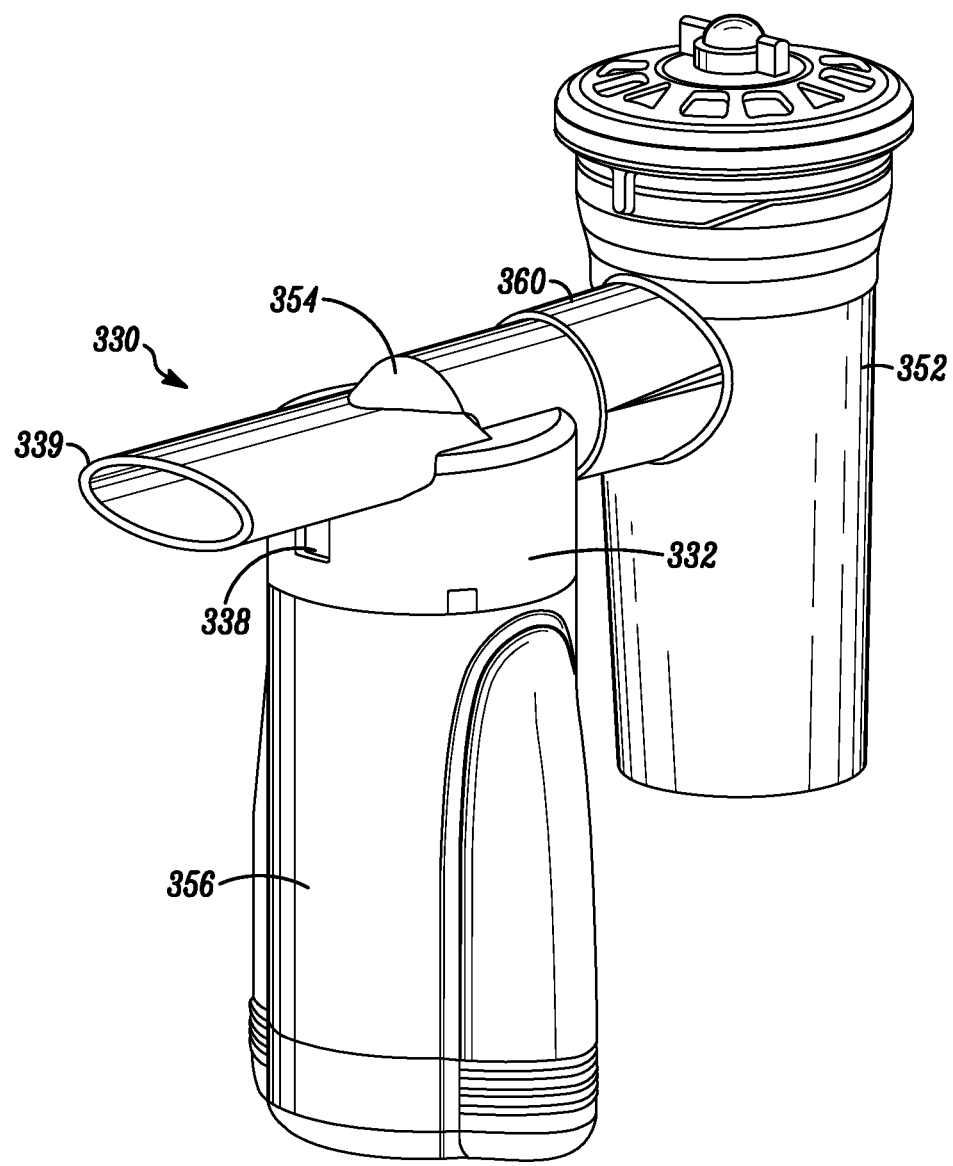
FIG. 7 is a perspective view of a third embodiment of an OPEP device attached to a nebulizer.
Figure 8:
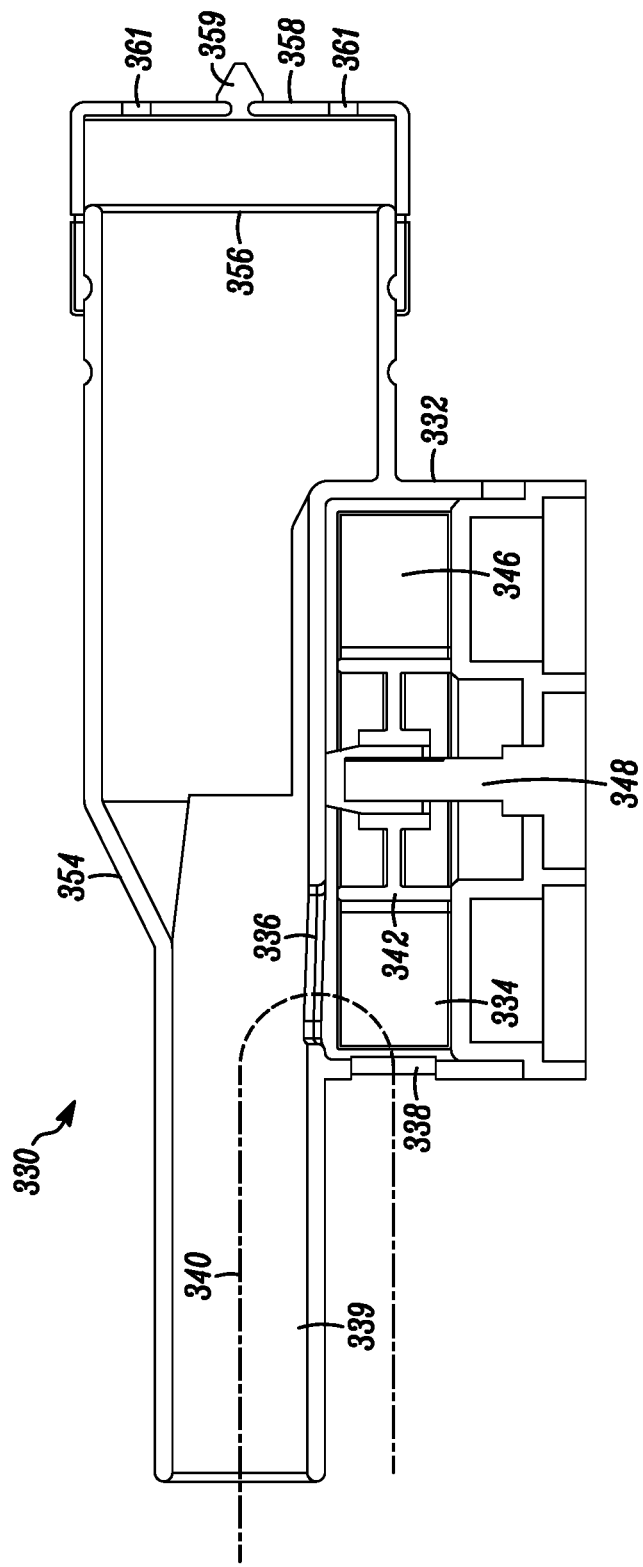
FIG. 8 is a cross-sectional side view of the embodiment of FIG. 7.

Referring to FIGS. 7-8, a third embodiment of an OPEP device 330 is shown. As shown in FIG. 7, the OPEP device 330 is adapted to connect to an output 360 of a nebulizer 352 for the simultaneous administration of OPEP and aerosol therapies. The OPEP device 330 generally includes a respiratory portal 354 for fluidly interconnecting the nebulizer 352, a mouthpiece 339, and the OPEP housing 332. The OPEP device 330 may be configured such that it can be used either in combination with the nebulizer 352 or solely for administration of OPEP therapy. FIG. 7 also illustrates a motor housing 356 for housing a motor (not shown) and batteries (not shown) for supplying power to the motor. A shaft 348 is provided to transfer rotational motion from the motor to the restrictor member 342.

Referring to FIG. 8, a side view of the respiratory portal 354 is shown without the nebulizer 352 for delivery of OPEP therapy only. In FIG. 8, the chamber inlet 336 is located above the interior chamber 334 and the chamber outlet 338 is located directly beneath the mouthpiece 339. However, it should be noted that the chamber inlet 336 and the chamber outlet 338 may be located elsewhere on the housing 332, as discussed in reference to the previous embodiments.

The respiratory portal 354 includes a nebulizer port 356 adapted for receiving either the nebulizer output 360 or an end cap 358 for regulating the flow of air through the nebulizer port 356. The end cap 358 and the nebulizer output 360 may be removably connected to the nebulizer port 356 by any means, including threaded or snap-on connections. Both the nebulizer output 360 and the end cap 358 may include a one-way valve 359 configured so that air may enter the respiratory portal 354 through the valve opening 361 on inhalation, but block the flow of air out of the valve opening 361 upon exhalation. Likewise, the chamber inlet 336 may include a one way valve (not shown) configured so that air may enter the interior chamber 334 through the chamber inlet 336 on exhalation, but be prevented from flowing out of the interior chamber 334 upon inhalation.

Thus, when a user of the OPEP device 330 exhales into the mouthpiece 339, the one way valve in the end cap 358 or nebulizer output 360 closes, the one way valve through the chamber inlet 336 opens, and exhaled air is forced into the interior chamber 334 through the chamber inlet 336. In contrast, when a user of the OPEP device 330 inhales air through the mouthpiece 339, the one way valve in the end cap 358 or nebulizer output 360 opens, the one-way valve through the chamber inlet 336 closes, and air is drawn through the nebulizer port 356 into the user's mouth. If the nebulizer 352 is attached, a user inhales medicated air drawn from the nebulizer 352 upon inhalation. Any of a number of commercially available nebulizers may be used. One suitable nebulizer is the AeroEclipse® II breath actuated nebulizer available from Trudell Medical International of London, Canada. Descriptions of suitable nebulizers may be found in U.S. Pat. No. 5,823,179, the entirety of which is hereby incorporated by reference herein.

As in the previously discussed embodiments, the OPEP device 330 administers OPEP therapy to the user during an exhalation period. As a user exhales into the mouthpiece 339, exhaled air is forced through the chamber inlet 336 and into the interior chamber 334. During exhalation, as the restrictor member 342 rotates, and as the blocking segments 346 pass by the chamber inlet 336, the exhalation pressure at the chamber inlet 336 oscillates between a minimum when the restrictor member 342 is an open position and a maximum when the restrictor member 342 is in a closed position.

Alternatively, the OPEP device 330 may also be configured to administer oscillating pressure therapy to the user during both inhalation and exhalation. If the end cap 358 is provided without a one-way valve, inhaled air is drawn from the interior chamber 334 through the chamber inlet 336. In such a configuration, as the restrictor member 342 rotates, and as the blocking segments 346 pass by the chamber inlet 336, the inhalation pressure at the chamber inlet 336 oscillates between a minimum when the restrictor member 342 is a closed position and a maximum when the restrictor member 342 is in an open position.

Figure 9:
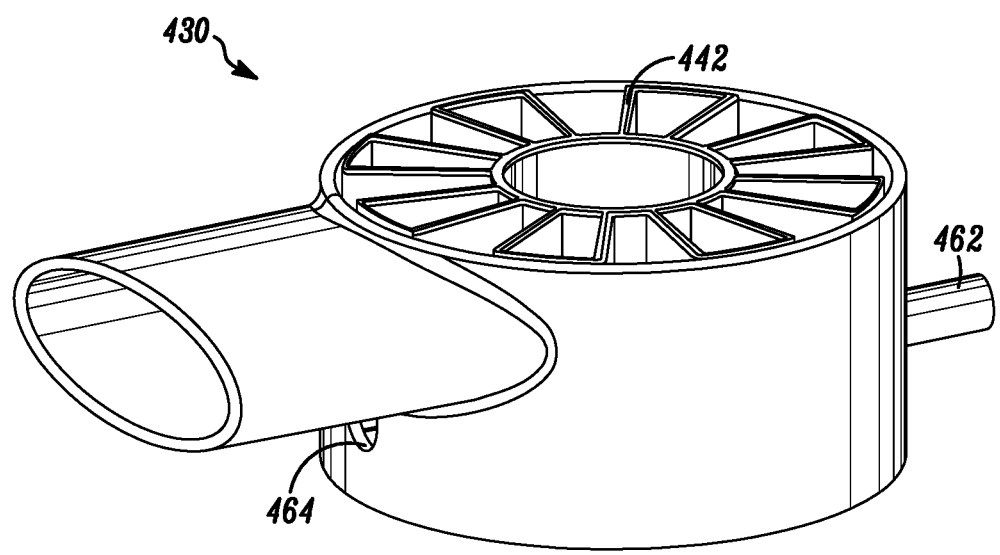
FIG. 9 is a perspective view of a fourth embodiment of an OPEP device with a top portion of the device's housing removed.

Referring to FIG. 9, a fourth embodiment of an OPEP device 430 is shown with a top portion of a housing 432 removed for purposes of illustration. The OPEP device 430 is adapted for connection to a compressed air source (not shown), which may be used to rotate a restrictor member 442. Because compressed air sources are commonly found in hospital settings, the use of compressed air to rotate the restrictor member 442 is convenient. The OPEP device 430 includes a compressed air inlet 462 for connecting to a compressed air hose (not shown) and an exhaust outlet 464 for discharging the compressed air.

Figure 10:
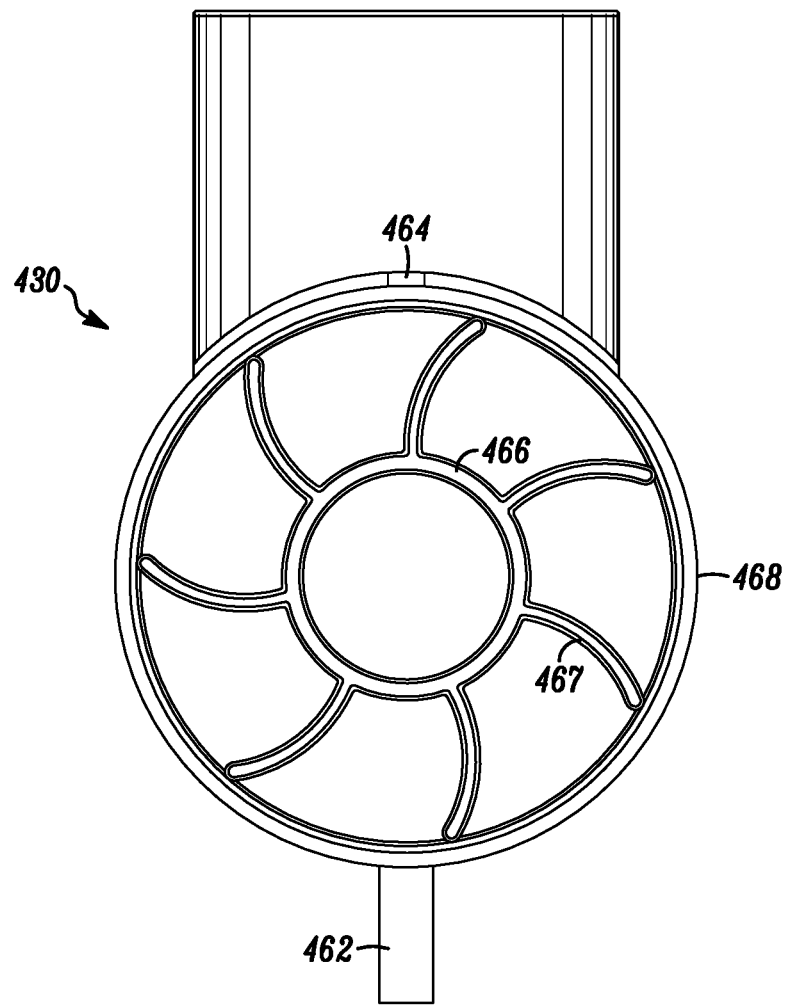
FIG. 10 is a bottom view of the embodiment of FIG. 9 with a bottom potion of the device's housing removed.

Referring to FIG. 10, a bottom view of the OPEP device 430 is shown with a bottom portion of housing 430 removed. A turbine 466 is rotatably mounted within a turbine housing 468 and includes a plurality of vanes 467 configured such that compressed air entering the compressed air inlet 462 causes the turbine 466 to rotate. As the turbine 466 rotates, the compressed air is discharged out the exhaust outlet 464.

Figure 11:
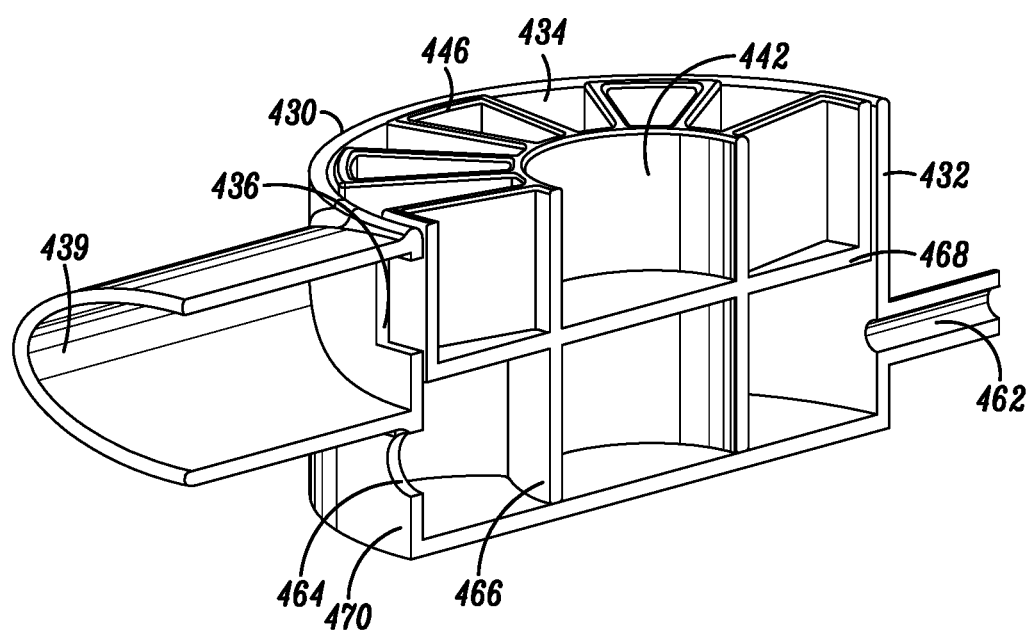
FIG. 11 is a cross-sectional perspective view of the embodiment of FIG. 9.

Referring to FIG. 11, a cross-sectional perspective view of the OPEP device 430 is shown with a top portion of the housing 432 removed. In this embodiment, a restrictor member 442 and the turbine 466 are joined together along a radial plane by a connecting member 468. Above the connecting member 468, a housing 432 surrounds the restrictor member 442 and defines an interior chamber 434. Below the connecting member 468, a turbine housing 470 surrounds the turbine 466 and includes the compressed air inlet 466 and the exhaust outlet 464. Although FIG. 11 illustrates the restrictor member 442 and the turbine 466 as being joined by the connecting member 468, it should be appreciated that the restrictor member 442 and the turbine 466 may be separate and operatively connected by other means, such as by a shaft. In such a configuration, the housing 432 and the turbine housing 470 may also be separate.

In operation, the OPEP device 430 administers OPEP therapy to a user when it is hooked up to a source of compressed air and a user exhales into a mouthpiece 439. As compressed air is forced into the turbine housing 470 through the compressed air inlet 462, the turbine 466 begins to rotate. Because the turbine 466 is connected to the restrictor member 442, rotation of the turbine 466 also causes the restrictor member 442 to rotate. As the restrictor member 442 rotates, and as blocking segments 446 pass by a chamber inlet 436, the exhalation pressure at the chamber inlet 436 oscillates between a minimum when the restrictor member 442 is an open position and a maximum when the restrictor member 442 is in a closed position.

Figure 12:
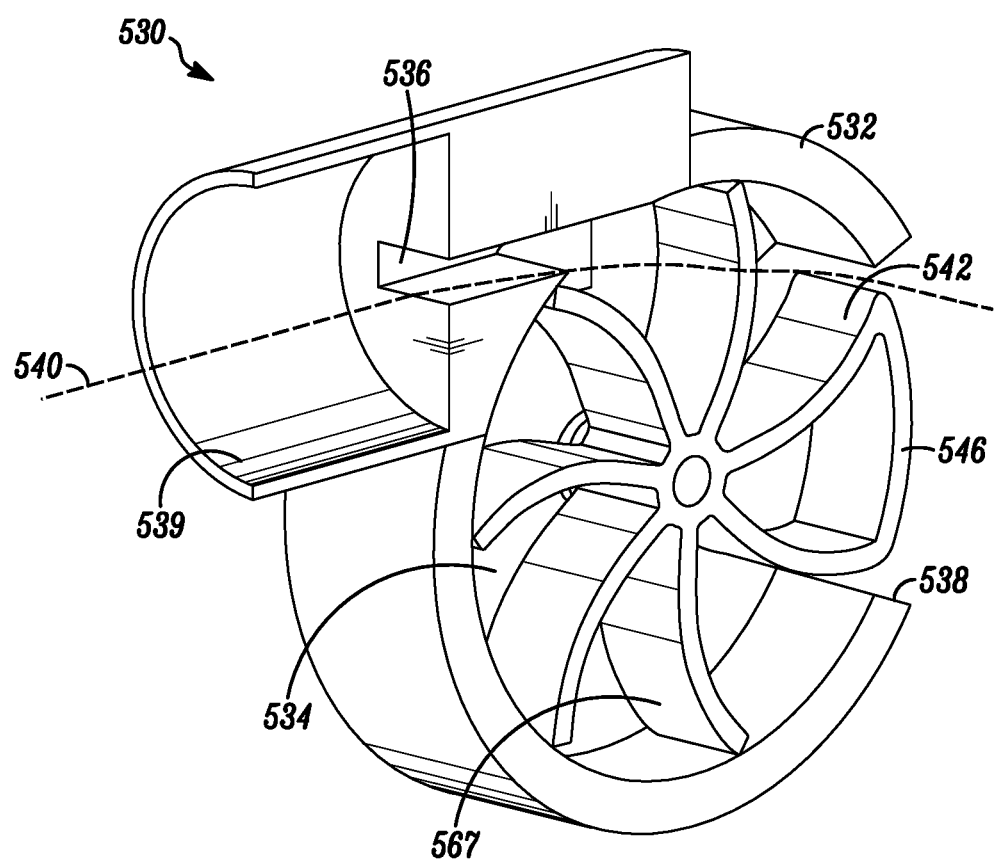
FIG. 12 is a cross-sectional perspective view of a fifth embodiment of an OPEP device.

Referring to FIG. 12, a cross-sectional perspective view of a fifth embodiment of an OPEP device 530 is shown. The OPEP device 530 is adapted to provide OPEP therapy using the force of air exhaled into the mouthpiece 539 to rotate the restrictor member 542, without the aid of a motor or compressed air. In general, the OPEP device 530 includes a housing 532, an interior chamber 534, a chamber inlet 536, a chamber outlet 538, an exhalation flow path 540, and a restrictor member 542.

The restrictor member 542 in the OPEP device 530 includes a plurality of vanes 567 adapted to rotate the restrictor member 542 when a user exhales into the mouthpiece 539. The restrictor member 542 also includes a blocking segment 546 formed between two adjacent vanes 567. Thus, when a user exhales into the mouthpiece 539, air is forced through the chamber inlet 536 and the restrictor member 542 begins to rotate. As the restrictor member rotates, and as the blocking segment 546 periodically passes by the chamber inlet 536, the exhalation pressure at the chamber inlet 536 oscillates between a minimum when the restrictor member 542 is in an open position and a maximum when the restrictor member 542 is in a closed position.

Figure 13:
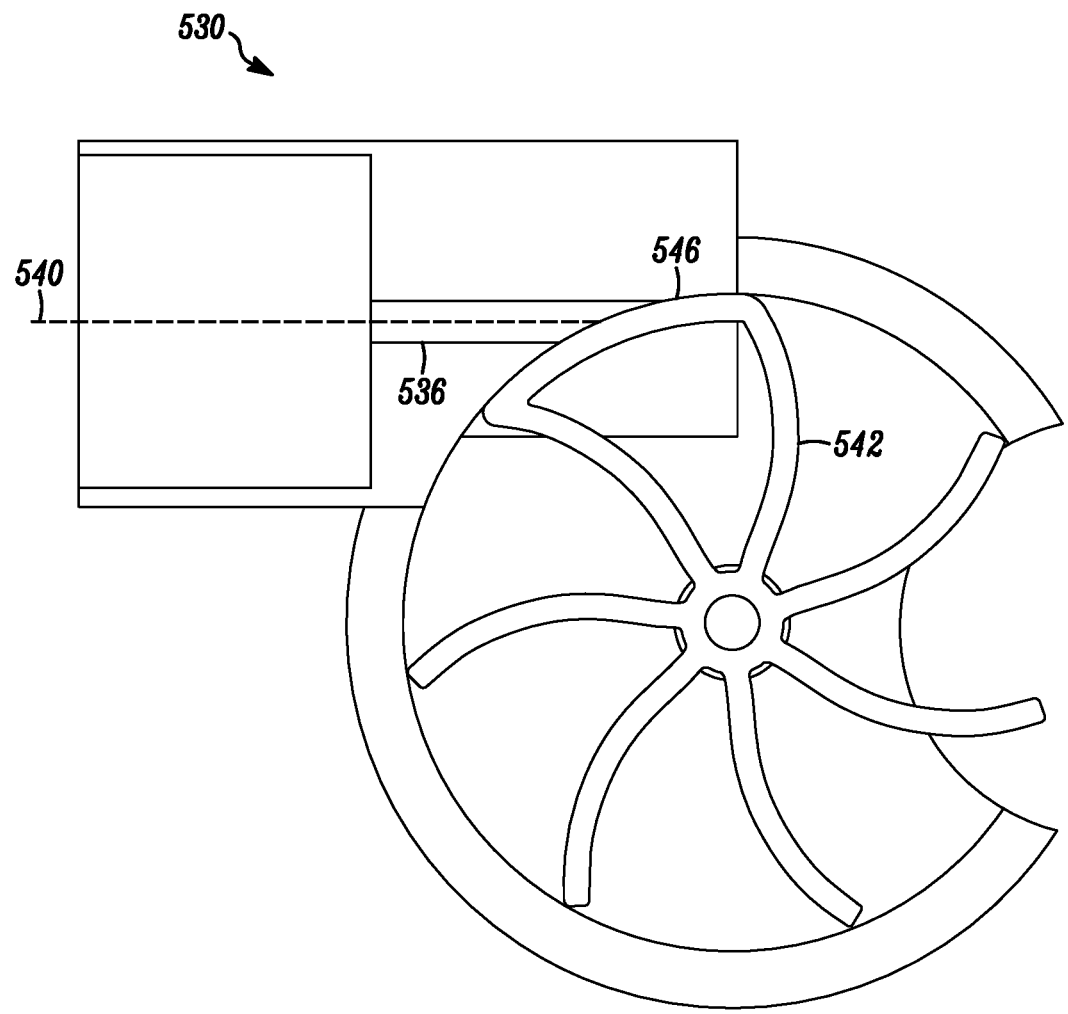
FIG. 13 is a cross-sectional side view of the embodiment of FIG. 12 showing a restrictor member in a closed position.

When the user stops exhaling into the OPEP device 530, the restrictor member 542 comes to a rest. As shown in FIG. 13, the restrictor member 542 may come to rest in a closed position where the blocking segment 546 is substantially blocking the flow path 540 through the chamber inlet 536. If the restrictor member 542 comes to rest in a closed position, a sufficient amount of exhaled air may not enter the interior chamber 534 to initiate the rotation of the restrictor member 542.

Figure 14:
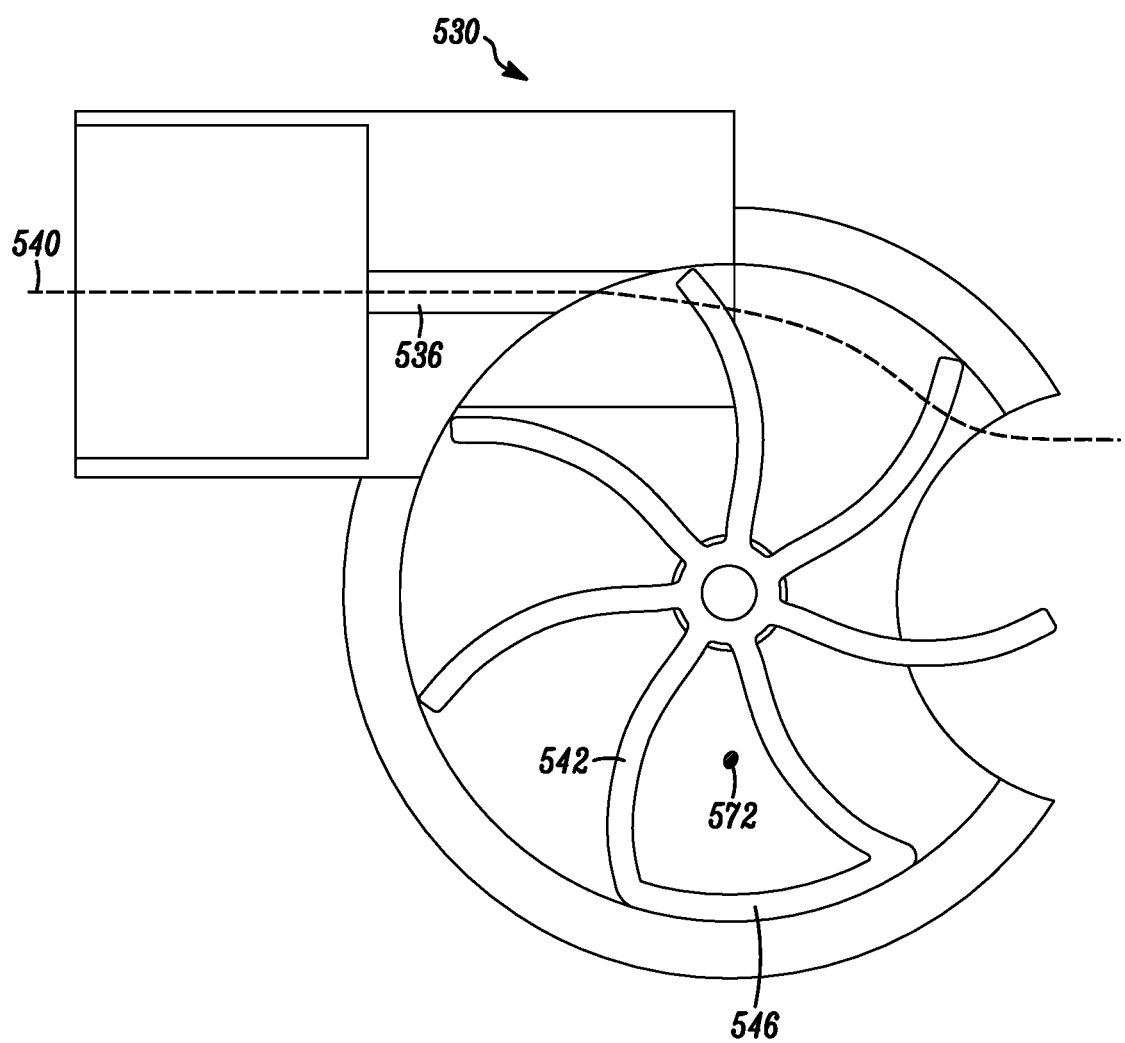
FIG. 14. is a cross-sectional side view of the embodiment of FIG. 12 showing a restrictor member in an open position.

As shown in FIG. 14, the restrictor member 542 may therefore be weighted to have a center of gravity 572 offset from its axis of rotation. Based on the location of the center of gravity 572 of the restrictor member 542, gravity may be used to ensure that the restrictor member 542 comes to rest in an open position when the OPEP device 530 is held upright.

Figure 15:
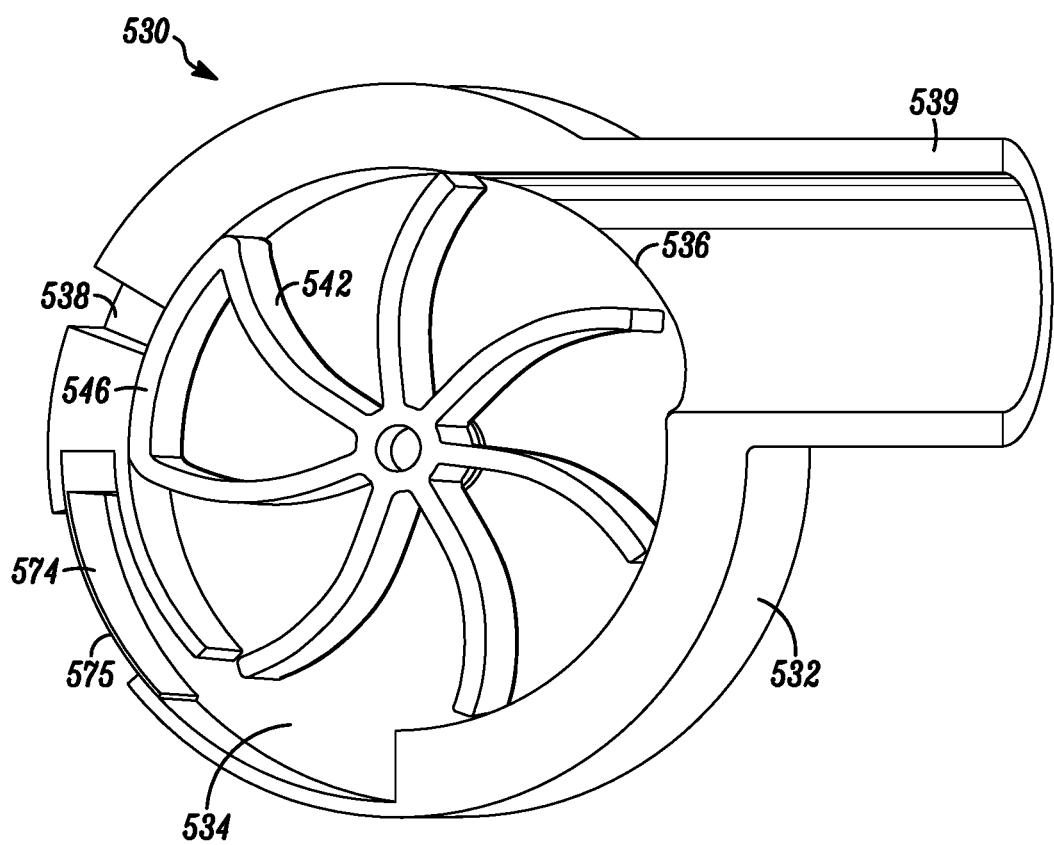
FIG. 15 is a cross-sectional perspective view of the embodiment of FIG. 12 having a one way-valve.
Figure 16A:
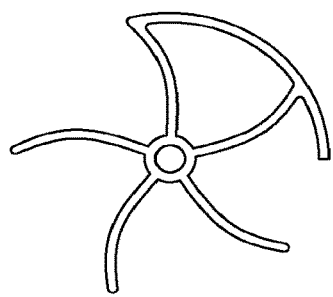
FIGS. 16A-C are top views of various restrictor members suitable for use in the embodiment of FIG. 12.
Figure 16B:
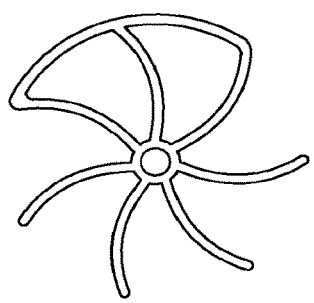
Figure 16C:
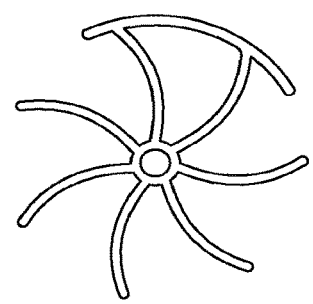
Figure 17:
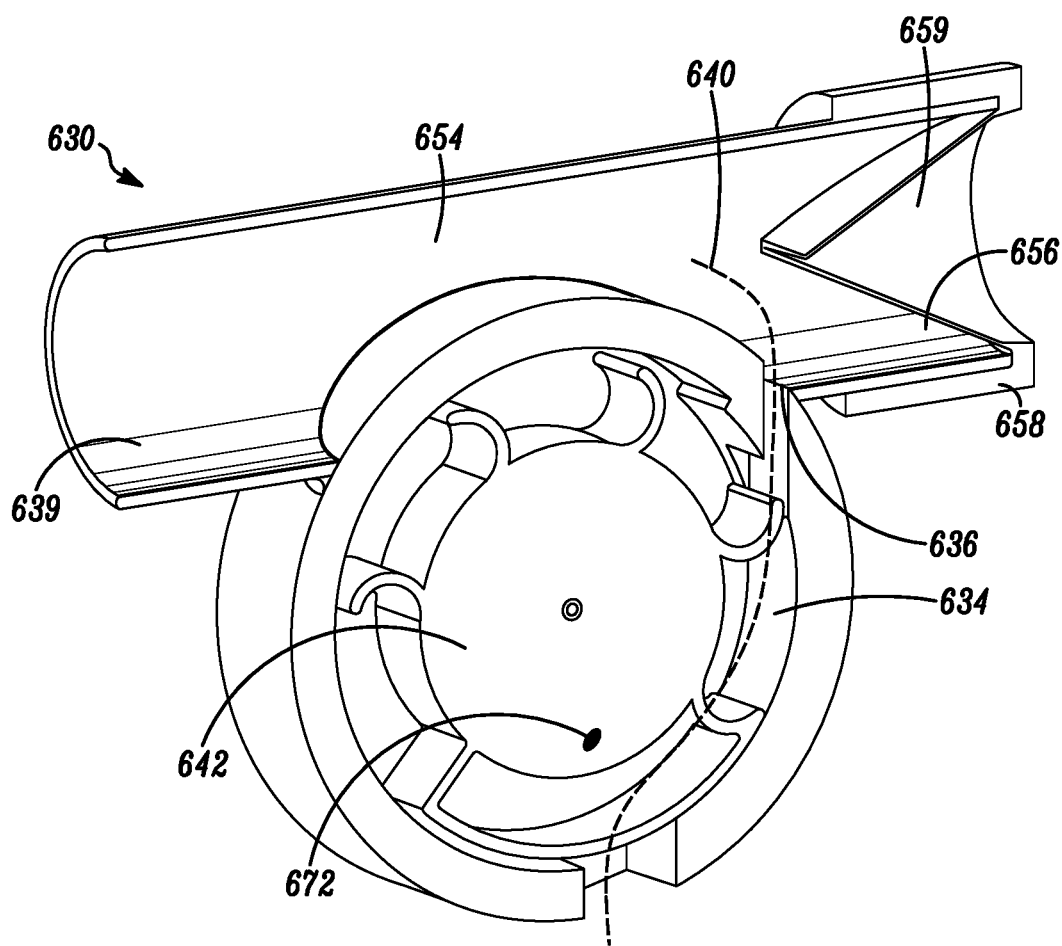
FIG. 17 is a cross-sectional perspective view of a sixth embodiment of an OPEP device; and, FIG. 18 is a cross-sectional perspective view of the embodiment of FIG. 17 attached to a nebulizer.
Figure 18:
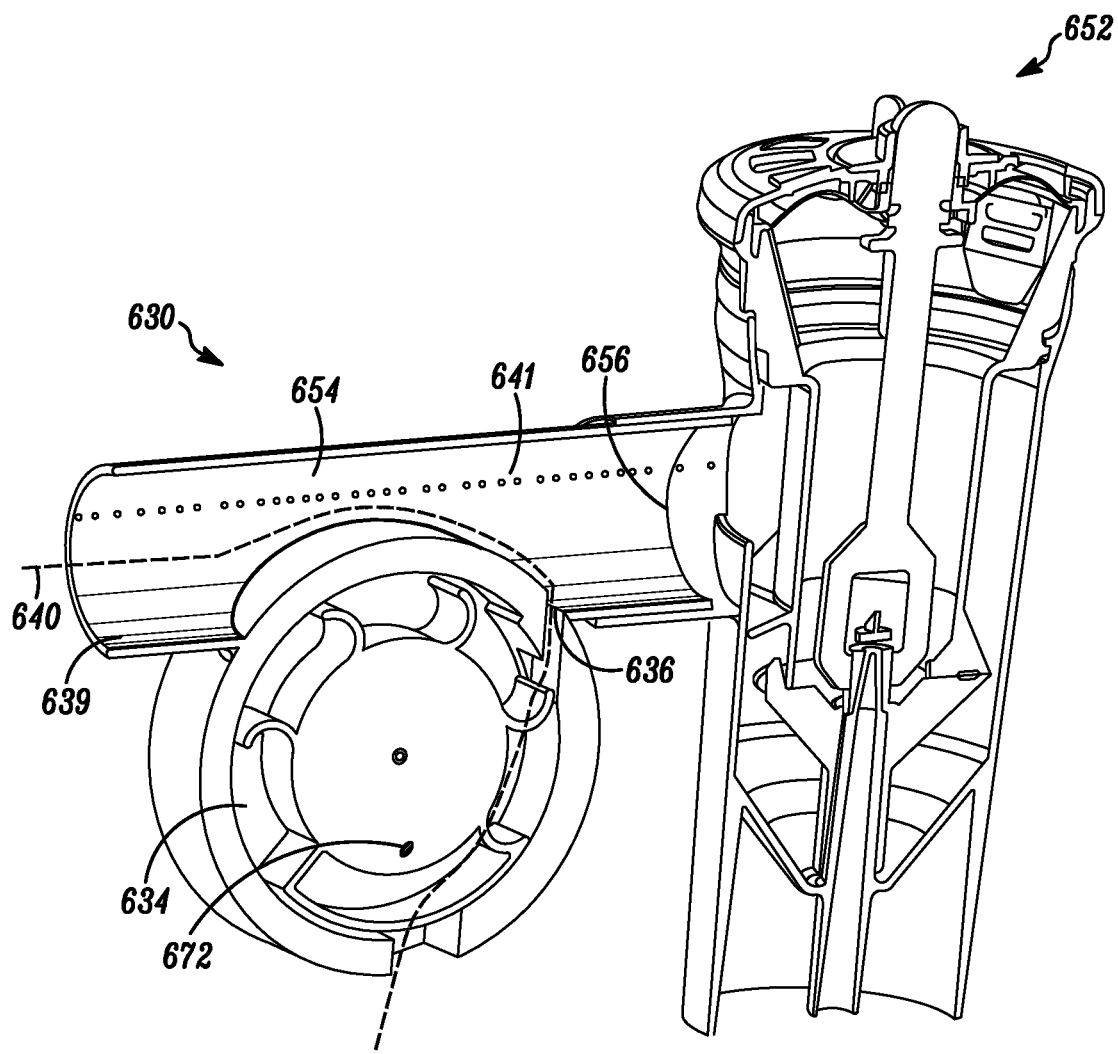

Alternatively, as shown in FIG. 15, the housing 532 of the OPEP device 530 may also include a one-way valve 574 configured to allow air to enter the interior chamber 534 through the valve opening 575 upon inhalation. The one-way valve 574 prevents air from exiting the interior chamber 534 during exhalation. In this configuration, the OPEP device 530 is adapted to restrict exhaled air flowing out of the interior chamber 534 at the chamber outlet 538. Thus, when a user exhales into the mouthpiece 539 and through the chamber inlet 536, the restrictor member 542 rotates, and the blocking segment 546 periodically restricts the flow of exhaled air through the chamber outlet 538. As the user exhales, the exhalation pressure at the chamber outlet 538 oscillates between a minimum and a maximum in the same manner as explained above, which is effectively transmitted back to the user for the administration of OPEP therapy. In this configuration, the chamber inlet 536 is large enough such that the blocking segment 546 does not substantially restrict the cross sectional area of the flow path 540 through the chamber inlet 536.

However, if the restrictor member 542 comes to rest in a position where the blocking segment 546 is restricting the flow of air through the chamber outlet 538, a sufficient amount of exhaled air may not pass along the exhalation flow path 540 through the chamber outlet 538 to initiate rotation of the restrictor member 542. In this situation, a user may inhale to open the one-way valve 574 and permit air to flow through the valve opening 575, into the interior chamber 534, and through the chamber inlet 536, thereby initiating rotation of the restrictor member 542, and moving the blocking segment 546 to a position where it is not restricting the flow of air through the chamber outlet 538. After the blocking segment 546 has moved to a position where it is not restricting the flow of air through the chamber outlet 538, a user may exhale to begin administration of OPEP therapy.

As in the previous embodiments, the housing 532 is preferably openable so that the housing 532 and the parts contained therein may be periodically accessed,

What is claimed is:

1. A respiratory treatment device comprising:
   an inlet configured to receive exhaled air into the device;
   an outlet configured to permit exhaled air to exit the device;
   an opening positioned along a flow path defined between the inlet and the outlet;
   and,
   a blocking segment configured to move relative to the opening in response to a flow of air along the flow path between a closed position, where the flow of air through the opening is restricted, and an open position, where the flow of air path through the opening is less restricted;

wherein there is an absence of a force biasing the blocking segment toward the closed position during a period when air is not flowing along the flow path; and, wherein a size of a blocking surface of a blocking segment is equal to or greater than a size of the opening.

2. The respiratory treatment device of claim 1, wherein the blocking segment is configured to move without delay in response to the flow of air along the flow path between the closed position and the open position.

3. The respiratory treatment device of claim 1, further comprising at least one vane positioned in the flow path and configured to move the blocking segment between the closed position and the open position in response to the flow of air along the flow path.

4. The respiratory treatment device of claim 1, wherein the blocking segment is rotatable about an axis of rotation perpendicular to a direction of the flow of air at a location in the flow path where the blocking segment is in the closed position.

5. The respiratory treatment device of claim 3, wherein the blocking segment and the at least one vane have a combined center of gravity offset from an axis of rotation about which the at least one vane is rotatably mounted.

6. The respiratory treatment device of claim 1, wherein the blocking segment is biased by a force of gravity toward the open position.

7. The respiratory treatment device of claim 1, wherein the device is an oscillating positive expiratory pressure treatment device.

8. The respiratory treatment device of claim 7, wherein the device is configured to administer oscillating positive expiratory pressure therapy regardless of a physical orientation of the device.

9. The respiratory treatment device of claim 1, wherein the flow of air through the opening is completely blocked when the blocking segment is in the closed position.

10. The respiratory treatment device of claim 1, wherein the blocking surface of the blocking segment contacts the opening when the blocking segment is in the closed position.

11. A respiratory treatment device comprising:
an inlet configured to receive exhaled air into the device;
an outlet configured to permit exhaled air to exit the device;
an opening positioned along a flow path defined between the inlet and the outlet;
and,
a blocking segment configured to move relative to the opening without delay in response to a flow of air along the flow path between a closed position, where the flow of air through the opening is restricted, and an open position, where the flow of air through the opening is less restricted;
wherein the blocking segment is biased by a force of gravity toward the open position; and,
wherein a size of a blocking surface of the blocking segment is equal to or greater than a size of the opening.

12. The respiratory treatment device of claim 11, wherein there is an absence of a force biasing the blocking segment toward the closed position during a period when air is not flowing along the flow path.

13. The respiratory treatment device of claim 11, further comprising at least one vane positioned in the flow path and configured to move the blocking segment between the closed position and the open position in response to the flow of air along the flow path.

14. The respiratory treatment device of claim 11, wherein the blocking segment is rotatable about an axis of rotation perpendicular to a direction of the flow of air at a location in the flow path where the blocking segment is in the closed position.

15. The respiratory treatment device of claim 13, wherein the blocking segment and the at least one vane have a combined center of gravity offset from an axis of rotation about which the at least one vane is rotatably mounted.

16. The respiratory treatment device of claim 11, wherein the device is an oscillating positive expiratory pressure treatment device.

17. The respiratory treatment device of claim 16, wherein the device is configured to administer oscillating positive expiratory pressure therapy regardless of a physical orientation of the device.

18. The respiratory treatment device of claim 11, wherein the flow of air through the opening is completely blocked when the blocking segment is in the closed position.

19. The respiratory treatment device of claim 11, wherein the blocking surface of the blocking segment contacts the opening when the blocking segment is in the closed position.

20. A respiratory treatment device comprising:
an inlet configured to receive exhaled air into the device;
an outlet configured to permit exhaled air to exit the device;
an opening positioned along a flow path defined between the inlet and the outlet;
and,
a blocking segment configured to move relative to the opening without delay in response to a flow of air along the flow path between a closed position, where the flow of air through the opening is restricted, and an open position, where the flow of air through the opening is less restricted; and,
at least one vane positioned in the flow path and configured to rotate the blocking segment between the closed position and the open position in response to the flow of air along the flow path;
wherein there is an absence of a force biasing the blocking segment toward the closed position during a period when air is not flowing along the flow path;
wherein the blocking segment is biased by a force of gravity toward the open position; and,
wherein a size of a blocking surface of the blocking segment is equal to or greater than a size of the opening.

21. The respiratory treatment device of claim 20, wherein the blocking segment is rotatable about an axis of rotation perpendicular to a direction of the flow of air at a location in the flow path where the blocking segment is in the closed position.

22. The respiratory treatment device of claim 20, wherein the blocking segment and the at least one vane have a combined center of gravity offset from an axis of rotation about which the at least one vane is rotatably mounted.

23. The respiratory treatment device of claim 20, wherein the respiratory treatment device is an oscillating positive expiratory pressure treatment device.

24. The respiratory treatment device of claim 23, wherein the respiratory treatment device is configured to administer oscillating positive expiratory pressure therapy regardless of a physical orientation of the respiratory treatment device.

25. The respiratory treatment device of claim 20, wherein the flow of air through the opening is completely blocked when the blocking segment is in the closed position.

26. The respiratory treatment device of claim 20, wherein the blocking surface of the blocking segment contacts the opening when the blocking segment is in the closed position.

* * * * *

UNITED STATES PATENT AND TRADEMARK OFFICE
CERTIFICATE OF CORRECTION

PATENT NO. : 10,668,235 B2  
APPLICATION NO. : 15/415524  
DATED : June 2, 2020  
INVENTOR(S) : Adam Meyer et al.

Page 1 of 1

It is certified that error appears in the above-identified patent and that said Letters Patent is hereby corrected as shown below:

In the Claims

Column 10, Claim 1, Line 66, delete "path"

Signed and Sealed this  
Twenty-first Day of July, 2020

Andrei Iancu  
*Director of the United States Patent and Trademark Office*